United States Patent [19]
Winter et al.

[11] 3,940,502
[45] Feb. 24, 1976

[54] FLAVORING AGENT

[75] Inventors: Max Winter, Geneva, Switzerland; Irving M. Goldman, Niantic, Conn.; Fritz Gautschi, Commugny, Switzerland; Ivon Flament, Geneva, Switzerland; Max Stoll, Geneva, Switzerland

[73] Assignee: Firmenich & Cie, Geneva, Switzerland

[22] Filed: June 24, 1974

[21] Appl. No.: 482,691

Related U.S. Application Data

[60] Division of Ser. No. 243,866, April 13, 1972, abandoned, which is a division of Ser. No. 70,560, Sept. 8, 1970, Pat. No. 3,702,253, which is a continuation of Ser. No. 543,069, April 18, 1966, abandoned, which is a continuation-in-part of Ser. No. 452,342, April 30, 1965, abandoned.

[52] U.S. Cl. .............................. 426/536; 260/347.8
[51] Int. Cl.² ................... A23L 1/226; A23L 1/234
[58] Field of Search ............. 426/65, 175, 193, 221, 426/222, 366, 536, 594; 260/347.8

[56] References Cited
UNITED STATES PATENTS
1,696,419 12/1928 Staudinger et al. ............. 426/65 X

OTHER PUBLICATIONS
JACS 49, 1065–1067 (1927).

*Primary Examiner*—A. Louis Monacell
*Assistant Examiner*—Esther L. Massung
*Attorney, Agent, or Firm*—Howard J. Newby; Thomas V. Sullivan; Bruno P. Struzzi

[57] ABSTRACT

The enchancement of foodstuffs is effected by the addition of a small but effective flavor-modifying amount of a compound having the general formula

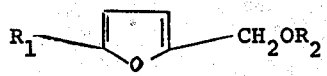

wherein $R_1$ and $R_2$ are hydrogen, alkyl, eg. methyl, ethyl; aryl; e.g. phenyl, alkylphenyl; furfuryl or alkylfurfuryl groups.

24 Claims, No Drawings

FLAVORING AGENT

This is a division of application Ser. No. 243,866 filed Apr. 13, 1972 now abandoned, which is a division of application Ser. No. 70,560 filed Sept. 8, 1970, now U.S. Pat. No. 3,702,253; which latter application is a continuation of now-abandoned application Ser. No. 543,069 filed Apr. 18, 1966, which is a continuation-in-part of now-abandoned application Ser. No. 452,342 filed Apr. 30, 1965.

The invention relates to flavor agents in general. More particularly the invention relates to chemical compounds or compositions which have been found to have utility in the alteration of flavor or flavor characteristics of substances, whether naturally occurring or synthetic. Still more particularly the invention relates to a group of chemical compounds which have been found to be useful in the area of flavor-note alteration, whether by the enhancement of flavors or flavor-notes that are characteristic in a substance, by the alteration of a flavor or a flavor-note from a less to a more desirable one, or by the complete or partial masking of a flavor or flavor-note.

As is generally recognized by those familiar with the art, the science of flavor technology is an extremely complex one. Although much is known about flavor and flavor technology there is still a great deal to be learned in the field and the body of scientific literature is being rapidly expanded by those working in the area. The technology of flavor synthesis and blending of various flavor elements to achieve certain desirable results is of great commercial importance at the present stage of industrial advance. Commercial production of consumer goods from synthetic starting materials is becoming more and more common, and desirable, as world population continues to increase its demands upon the finite capacity for the production of natural products. Industry is also continually seeking means of upgrading natural products — methods of altering or enhancing the qualities of taste of less desirable natural products — usually more abundant — into more desirable product qualities. Often, for example, a product can be made commercially attractive only by masking or blanking out an undesirable flavor component. Formerly, before the advent of the flavor chemist and his technology, this unit of production would have been lost, or at least, would have had to have been re-processed to a useable quality. By the use of specifically designed flavoring agents, however, the undesirable flavor note can be eliminated or masked with another desirable one, and the expensive and time-consuming re-processing step eliminated or the production batch saved for use. Too, it is common in some segments of the industry, particularly the food industry, to add flavor agents to production units to enhance or bring out a desirable flavor characteristics of products 13 and by so doing to render the product more desirable from a consumer preference standpoint.

It is the object of this invention therefore, to provide the flavor technologist with additional tools for his use in the alteration of food flavors, whether it be flavor or flavor-note alteration generally or the enhancement or improvement of flavor or flavor notes specifically.

It is a further object of the invention to furnish a group of chemical compositions which have utility in the technology of flavor alteration, whether added to solid or liquid compositions for human consumption, and which may be used in either solid or liquid form.

A further object of the invention is to describe a group of chemical compounds having desirable utility as flavor agents which may be prepared synthetically, thus enabling the food technologist to alter or enhance his product without drawing upon a natural product for the flavor agent.

A still further object of the invention is to describe a group of chemical compounds capable of synthesis from readily available organic substances which may be used singly or in combination to alter the flavor or flavor notes of compositions for food use, whether used in micro-quantities such as parts-per-million or in larger quantities, as the dictates of the end results may require.

Other objects will become apparent to those skilled in the art as the description proceeds.

Thus, in accordance with the concept of the instant invention, there is set out below a group of compounds which have been found to have utility as flavor agents and to represent valuable materials to the food technologist who wishes to alter the flavor components of foods or food products either liquid foods or beverages, such as fruit and vegetable juices, milk, coffee, tea, cocoa, chocolate, and the like or solid foods such as cereals, flours, confections, vegetables, meats, etc. The flavor agents may be used either in liquid or solid form and are used in quantities designed to give the desired results, as will be more clearly explained as the description proceeds.

The chemical compounds which have been found to have utility as flavor agents may be generally classified as furan ether compounds.

The flavor agents or flavor modifying compositions of this invention are available to the food technologists in a variety of forms. It is usually preferable to use the agents in the form of a solution, for ease of dilution, exactitude of measurement, efficiency of distribution in the end use, etc. However the chemical nature of the compound, its solubility in acceptable solvents, its stability, and other characteristics may dictate the form in which it is used.

The amounts of the agents used is also subject to wide variation, of course. More concentrated materials, and those with the greatest degree of flavor modifying ability will be used in lesser amounts. Some degree of experimentation is, of course, required to achieve the desired results. A small, but flavor modifying amount, of the agents is blended with the material whose total flavor is to be altered, the amount depending upon the end result desired.

Two different types of methods were used in testing the compounds listed in this specification for their utility as flavor agents, flavor modifiers, flavor alteration agents, flavor-note enhancers, and the like. The first type method (A) served the purpose of determining the intrinsic taste, flavor and aroma of each individual compound. The second type methods (B) and (C) were used for testing the flavor- and aroma- modifying or -enhancing effects of the compounds hereinafter listed on coffee products and more particularly on spray-dried soluble coffee products commercially known as "instant coffee."

METHOD A

The vehicle used for testing the flavor compounds was a 65% solution of cane sugar in tap water. The flavor compounds were incorporated in this sugar syrup in the form of 1% or 1 per 1,000 by weight solutions in 96% ethyl alcohol. The concentration of the flavor compounds in the sugar syrup varied between about 0.005 and 5 g. for 100 liters of syrup according to the varying strength of flavor compounds. Samples of each flavored sugar syrup were submitted to the members of the testing panels. After tasting the samples each member had to give an evaluation of each flavor compound in terms of descriptive words.

In the evaluation of materials for the alteration or enhancement of coffee flavor or of coffee flavor notes it is essential that the equipment used, coffee pots, cups, spoons, measuring equipment, etc. be absolutely clean prior to use.

METHOD B

The coffee base was prepared by dissolving 1 g. of a commercial spray-dried soluble coffee in boiling water. A sufficient number of pots was prepared to provide one pot for each flavor agent to be evaluated plus one control. The flavor agent was added to the coffee base in the form of a 1% or 1 per 1,000 by weight alcoholic solution at concentrations varying between 0.005 and 5 g. of flavor agent for 100 liters of coffee base. The measured quantity of the flavor agent was added to a pot of the coffee base material, stirred well, and poured immediately into cups for the organoleptic evaluation. The taste tests were made within a short time (not more than 15 minutes) after the final composition to be tested was prepared.

The organoleptic evaluation involved grading a series of cups that were coded, the taster merely rating the coded cups against the standard or control which did not contain the flavor agent. The standard was placed at the first position in a series of cups. The tasters were asked to ascertain whether or not there existed differences in the flavor of the samples to be tested as compared with the control. The tasters were furthermore asked to describe and characterize the various flavor notes and types determined.

METHOD C

Using boiling Crystal Spring Water, to provide a clean starting taste, a 1.35% solution of relatively bland tasting commercially available spray-dried soluble coffee was prepared. The containers used — preferably the lower portion of a glass coffee maker — was absolutely clean, as was the other equipment used, e.g. cups and spoons.

A sufficient number of containers, or pots, were used to accomodate each flavor fraction to be studied, plus one control. The flavor fraction was measured carefully with a micro-syringe, adding from 2 to 150 microliters of the flavor fraction per pot. The mixture of coffee solution and flavor fraction was stirred and immediately poured into cups for tasting. At least 5 experienced tasters are used. The tasting should begin at least within 15 minutes after the solution is prepared. If not, the solution should be discarded and fresh solution prepared.

The cups are coded and the samples are not identified. A standard sample is included in which no flavor fraction has been added. The taster is asked to identify and describe the flavor enhancement or modification noted.

In the following specific description of the furan ether compounds there is first given the structural formula followed by a list of members of the group which have been found to have outstanding utility in the concept of this invention. Immediately following the chemical name of each member there is given the commercial source or a literature reference giving a method for its preparation. Commercially available products will be identified by the abbreviation c.a., and may be obtained from FLUKA, A.G., Buchs S.G., Switzerland; ALDRICH CHEM. CO., Milwaukee, Wis.; DR.F. RASCHIG GMBH, Ludwigshafen a. Rh., West-Germany; or K & K LABORATORIES INC., Plainview, N.Y. 11803.

In those instances wherein new compounds are described a detailed method of preparation is given following the list of the group members. New compounds will be identified by the abbreviation n.c.

I. — FURAN ETHERS

The compounds of this group have the general formula:

(1)

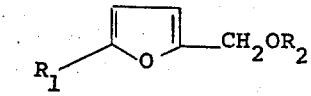

wherein $R_1$ and $R_2$ are hydrogen; alkyl, e.g. methyl, ethyl; aryl, e.g. phenyl, alkylphenyl; furfuryl, or alkylfurfuryl groups.

Compounds representative of this group include the following:

| | | |
|---|---|---|
| (1) a. | furfuryl methyl ether | Ber. 56,1004 (1923) |
| b. | furfuryl ethyl ether | Ber. 56,1004 (1923) |
| c. | furfuryl phenyl ether | Bull. 1938, 1151 |
| d. | 5-methyl-furfuryl furfuryl ether | n.c. |
| e. | difurfuryl ether | Am.Soc. 49,1006 (1927) |

(1) d. 5-Methyl-furfuryl furfuryl ether was prepared by the procedure described by J. E. Zanetti in J.Am.-Chem.Soc. 49, 1066 (1927) for the difurfuryl ether, starting with 5-methyl-furfuryl bromide (Compt.Rend. 222, 1441 (1946)) instead of furfuryl bromide of Zanetti. The product was isolated by ether extraction of the crude mixture after having diluted with water. For purification the ether extract was distilled twice - b.p. 68°–70°C. at 0.01 mm./Hg vacuum. The product was a viscous colourless liquid, darkening rapidly on contact with air.

ORGANOLEPTIC EVALUATIONS

As was described above, the compounds of this invention were subjected to organoleptic evaluation tests either in a syrup base (A), or one of the two soluble coffee bases (B and C). The following table give the results of these organoleptic evaluations. In the table, the Roman numeral refers to the number of the group from which the test compounds were selected. The column headed "Number" refers to the number of the test compound of the corresponding group. The column headed "Test" gives the Method of the Test, as described hereinbefore, and the column headed "Quantity" sets out the amount of the Test Compound used in grams per 100 liters of the base material.

TABLE I

| Number | Test | Quantity | Organoleptic Characterization |
|---|---|---|---|
| (1)a. | A | 1.0 | strong mustard taste |
| (1)a. | B | 1.0 | nutty, coffee grounds-like |
| (1)a. | C | 0.27 | sulfury, rioy, phenolic taste |

TABLE I-continued

| Number | Test | Quantity | Organoleptic Characterization |
|---|---|---|---|
| (1)b. | A | 1.0 | mustard taste |
| (1)b. | C | 0.08 | buttery, groundsy taste |
| (1)c. | A | 0.25–0.5 | honey-like |
| (1)c. | B | 1.0 | coffee-grounds note |
| (1)c. | C | 0.04 | rye bread, caraway seed-like |
| (1)d. | A | 1.0 | green, water-cress like |
| (1)d. | C | 0.68 | earthy, mushroom like |
| (1)e. | A | 1.0 | salicylate, coffee-like |
| (1)e. | C | 0.14 | mushroom-like |

As has been stated above the compounds having utility in the concept of this invention may be added to substances in varying amounts to alter or to modify the flavor of the substance by masking or blanking out undesirable flavors, by enhancing or fortifying desirable flavor or flavor notes, or by adding to the original substance an entirely new and different flavor. As will also be apparent to those skilled in the art various mixtures or blends of the flavor agents described may be used to achieve a desired flavor or flavor note. If, for example, one wishes to enhance a certain flavor note, or group of flavor notes present in a substance such as coffee, one needs only mix together certain of the described flavor agents to obtain the desired result.

It should be kept in mind, as will be appreciated by those skilled-in-the-art, that with many flavors it is possible to imitate the natural flavor by selecting a limited number of the flavor enhancing substances examplified above. Coffee aroma, on the other hand, is much more complex than the ordinary flavoring materials and may necessitate the combination of many more of the examplified ingredients for reproduction.

It will also be understood that whereas the preferred embodiment of this invention is directed toward the enhancement or modification of coffee flavors, the concept of the invention has much wider application. While some of the compounds may be characterized by terms which are not directly related to coffee flavors, these compounds, when used in more complex formulas, may contribute desirable flavor notes to the overall flavor and aroma.

To summarize briefly this invention relates to a group of chemical compounds which have been found to have utility for the alteration or modification of the flavor of other materials. These compounds, called flavor agents or flavor modifiers, may be used in minute quantities to enhance the natural flavor of substances to which they are added, or to alter or modify a flavor which is undesirable, or to impart to a substance additional or different flavors or flavor notes. The flavor agents of the invention are used in minor, but flavor altering amounts, in any case, in quantities sufficient to obtain the desired results. The flavor modifiers are of particular importance and usefulness in the modification, alteration or enhancement of the flavor of coffee beverages made from soluble coffee and the preferred embodiment of the invention contemplates their use in conjunction with such products.

The flavor agents of the invention may be added at a convenient step in the soluble coffee process such as plating the dried soluble coffee with a desired dilution of the flavor agent in an acceptable solution followed by drying. In certain instances the desired agent may be added directly to a concentrated coffee extract and the mixture dried into a soluble coffee product which contains the flavor agent as an integral part thereof. Other methods of incorporation of the agents will suggest themselves to those skilled in the art and may, of course, be used without departing from the inventive concept, which may be described as being a composition of matter comprising a combination of a soluble coffee product, however prepared, whether liquid or solid, concentrated or dilute, which contains combined therewith a minor, but flavor modifying amount, of a flavor agent as described herein.

What is claimed is:

1. As a new composition of matter of soluble coffee material having added thereto a minor, but flavor-modifying amount of a compound selected from the group consisting of furfuryl methyl ether, furfuryl ethyl ether, furfuryl phenyl ether, difurfuryl ether and mixtures thereof.

2. The soluble coffee of claim 1 wherein the added compound is furfuryl methyl ether.

3. The soluble coffee of claim 1 wherein the added compound is furfuryl ethyl ether.

4. The soluble coffee of claim 1 wherein the added compound is furfuryl phenyl ether.

5. The soluble coffee of claim 1 wherein the added compound is difurfuryl ether.

6. A process for the alteration of the natural flavor of soluble coffee material which comprises adding thereto a minor, but flavor-modifying amount of a compound selected from the group consisting of furfuryl methyl ether, furfuryl ethyl ether, furfuryl phenyl ether, difurfuryl ether and mixtures thereof.

7. The process of claim 6 wherein the added compound is furfuryl methyl ether.

8. The process of claim 6 wherein the added compound is furfuryl ethyl ether.

9. The process of claim 6 wherein the added compound is furfuryl phenyl ether.

10. The process of claim 6 wherein the added compound is difurfuryl ether.

11. A composition selected from the group consisting of foodstuffs and beverages to which has been added an effective flavor-improving amount of a compound selected from the group consisting of furfuryl methyl ether, furfuryl ethyl ether, furfuryl phenyl ether, difurfuryl ether and mixtures thereof.

12. The composition of claim 11 wherein the added compound is furfuryl methyl ether.

13. The composition of claim 11 wherein the added compound is furfuryl ethyl ether.

14. The composition of claim 11 wherein the added compound is furfuryl phenyl ether.

15. The composition of claim 11 wherein the added compound is difurfuryl ether.

16. A process for the alteration of the flavor of a composition selected from the group consisting of foodstuffs and beverages which comprises adding thereto a minor, but flavor-modifying amount of a compound selected from the group consisting of furfuryl methyl ether, furfuryl ethyl ether, furfuryl phenyl ether, difurfuryl ether and mixtures thereof.

17. The process of claim 16 wherein the added compound is furfuryl methyl ether.

18. The process of claim 16 wherein the added compound is furfuryl ethyl ether.

19. The process of claim 16 wherein the added compound is furfuryl phenyl ether.

20. The process of claim 16 wherein the added compound is difurfuryl ether.

21. As a new composition of matter a soluble coffee material having added thereto a minor, but flavor-modifying amount of 5-methyl-furfuryl furfuryl ether.

22. A process for the alteration of the natural flavor of soluble coffee material which comprises adding thereto a minor, but flavor-modifying amount of 5-methyl-furfuryl furfuryl ether.

23. A composition selected from the group consisting of foodstuffs and beverages to which has been added thereto an effective flavor-modifying amount of 5-methyl-furfuryl furfuryl ether.

24. A process for the alteration of the flavor of a composition selected from the group consisting of foodstuffs and beverages which comprises adding thereto a minor, but flavor-modifying amount of 5-methyl-furfuryl furfuryl ether.

* * * * *